(12) United States Patent
Gjorstrup

(10) Patent No.: US 9,987,244 B2
(45) Date of Patent: *Jun. 5, 2018

(54) METHODS OF TREATING OTOTOXICITY

(71) Applicant: Anida Pharma Inc., Cambridge, MA (US)

(72) Inventor: Per Gjorstrup, Cambridge, MA (US)

(73) Assignee: ANIDA PHARMA, INC., Cambridge, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/274,529

(22) Filed: Sep. 23, 2016

(65) Prior Publication Data

US 2017/0105957 A1     Apr. 20, 2017

Related U.S. Application Data

(63) Continuation of application No. 14/771,158, filed as application No. PCT/US2014/018721 on Feb. 26, 2014, now Pat. No. 9,468,620.

(60) Provisional application No. 61/770,629, filed on Feb. 28, 2013.

(51) Int. Cl.
   *A61K 31/202*  (2006.01)
   *A61K 9/00*    (2006.01)

(52) U.S. Cl.
   CPC .......... *A61K 31/202* (2013.01); *A61K 9/0046* (2013.01)

(58) Field of Classification Search
   None
   See application file for complete search history.

(56) References Cited

U.S. PATENT DOCUMENTS

| | | | |
|---|---|---|---|
| 4,522,811 | A | 6/1985 | Eppstein et al. |
| 7,709,669 | B2 | 5/2010 | Serhan et al. |
| 7,759,395 | B2 | 7/2010 | Serhan et al. |
| 7,782,152 | B2 | 8/2010 | Darabi et al. |
| 8,273,792 | B2 | 9/2012 | Serhan et al. |
| 9,468,620 | B2 | 10/2016 | Gjorstrup |
| 2003/0191064 | A1 | 10/2003 | Kopke |
| 2009/0156673 | A1 | 6/2009 | Serhan et al. |
| 2010/0009952 | A1 | 1/2010 | Lichter et al. |
| 2012/0059061 | A1 | 3/2012 | Arita et al. |

FOREIGN PATENT DOCUMENTS

| | | |
|---|---|---|
| EP | 2 415 748 A1 | 2/2012 |
| JP | 2009-523414 A | 6/2009 |
| WO | WO-98/14182 A1 | 4/1998 |
| WO | WO-2007/071733 A2 | 6/2007 |
| WO | WO-2007/071733 A3 | 6/2007 |
| WO | WO-2009/137400 A2 | 11/2009 |
| WO | WO-2010/091226 A1 | 8/2010 |
| WO | WO-2010/095706 A1 | 8/2010 |

OTHER PUBLICATIONS

Halapin, N.A. et al. (Dec. 2010, e-published Dec. 7, 2010). "NPD1 induction of retinal pigment epithelial cell survival involves PI3K/Akt phosphorylation signaling," *Neurochem Res* 35(12):1944-1947.
International Search Report dated May 21, 2014, for PCT Application No. PCT/US2014/018721, filed Feb. 26, 2014, 3 pages.
Marcheselli, V.L. et al. (Jan. 2010). "Neuroprotectin D1/protectin D1 stereoselective and specific binding with human retinal pigment epithelial cells and neutrophils," Prostaglandins *Leukots Essent Fatty Acids* 82(1):27-34.
Patani, G.A. et al. (Dec. 19, 1996). "Bioisosterism: A Rational Approach in Drug Design," *Chem Rev* 96(8):3147-3176.
Serhan, C.N. et al. (Aug. 26, 2011). "Novel proresolving aspirin-triggered DHA pathway," *Chem Biol* 18(8):976-987.
Written Opinion dated May 21, 2014, for PCT Application No. PCT/US2014/018721, filed Feb. 26, 2014, 3 pages.
Yang, R. et al. (Sep. 9, 2011, e-published Jul. 12, 2011). "Decoding functional metabolomics with docosahexaenoyl ethanolamide (DHEA) identifies novel bioactive signals," *J Biol Chem* 286(36):31532-31541.

*Primary Examiner* — Heidi Reese
(74) *Attorney, Agent, or Firm* — Mintz Levin Cohn Ferris Glovsky and Popeo P.C.

(57) ABSTRACT

The present invention relates to use of DHA analogs and their pharmaceutical compositions for treating ototoxicity, by administering these compounds or pharmaceutical compositions to subjects in need thereof. Ototoxicity is defined as damage to the structures of the ear, such as the cochlea and vestibular system, by drugs or toxins. Ototoxicity can result in irreversible hearing loss, tinnitus, dysequilibrium, Meniere's disease, or vertigo.

10 Claims, 5 Drawing Sheets

METHODS OF TREATING OTOTOXICITY

CROSS REFERENCE TO RELATED APPLICATIONS

This application is a continuation of U.S. patent application Ser. No. 14/771,158, now U.S. Pat. No. 9,468,620, filed Aug. 27, 2015, which is a national stage entry under 35 U.S.C. § 271 of International Patent Application No. PCT/US2014/018721, filed Feb. 26, 2014, which, in turn, claims priority to and benefit of U.S. provisional patent application 61/770,629, filed on Feb. 28, 2013, the contents of each of which are incorporated herein by reference in its entirety.

BACKGROUND OF THE INVENTION

Ototoxicity is defined as damage to the structures of the ear, such as the cochlea and vestibular system, by drugs or toxins. Ototoxicity can result in irreversible hearing loss, tinnitus, dysequilibrium, Ménière's disease, or vertigo. There are more than 200 known pharmacologic agents that are known to cause ototoxicity, many of which are commonly used to treat bacterial infections, cancer, and heart disease. Currently, other than withdrawal from ototoxic medications which may not be a viable option for some patients, there are no known treatments to prevent, reduce, or ameloriate ototoxicity.

Accordingly, compounds and methods for treating ototoxicity are needed. The present invention addresses these needs.

SUMMARY OF THE INVENTION

The present invention provides, in part, a method for treating ototoxicity. The method includes administering to a subject in need thereof a therapeutically effective amount of a compound of Formula I, II, III or IV:

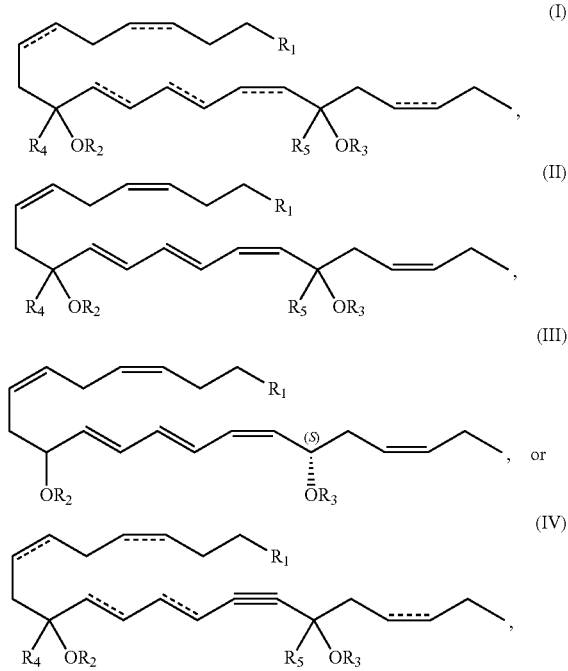

or a pharmaceutically acceptable salt, ester, solvate, hydrate or prodrug thereof. In Formula I, II, III, or IV:

═══ represents a cis or trans bond;

$R_1$ is —C(O)O$R_a$, —C(O)N$R_b R_c$, —C(O)H, —C(NH)N$R_b R_c$, —C(S)H, —C(S)O$R_a$, —C(S)N$R_b R_c$, or CN;

$R_2$ and $R_3$ are each independently H or a protecting group;

$R_4$ and $R_5$ are each independently H, halo, unsubstituted or substituted $C_1$-$C_6$ alkyl, unsubstituted or substituted $C_3$-$C_{10}$ carbocycle, unsubstituted or substituted heterocycle comprising one or two 3-, 4-, 5- or 6-member rings and 1-4 heteroatoms selected from N, O and S.

$R_a$ is a protecting group or -$T_1$-$Q_1$;

$R_b$ and $R_c$ are each independently a protecting group or -$T_1$-$Q_1$, or $R_b$ and $R_c$, together with the nitrogen atom to which they are attached, form an unsubstituted or substituted heterocycle comprising one or two 5- or 6-member rings and 1-4 additional heteroatoms selected from N, O and S;

$T_1$ is a bond or unsubstituted or substituted $C_1$-$C_6$ alkyl linker; and $Q_1$ is H, hydroxyl, halogen, unsubstituted or substituted $C_1$-$C_6$ alkyl, unsubstituted or substituted $C_1$-$C_6$ alkoxy, unsubstituted or substituted 2-6 membered heteroalkyl, unsubstituted or substituted $C_3$-$C_{10}$ carbocycle, or unsubstituted or substituted heterocycle comprising one or two 3-, 4-, 5- or 6-member rings and 1-4 heteroatoms selected from N, O and S.

The present invention also provides a method for treating ototoxicity by administering to a subject in need thereof a therapeutically effective amount of a pharmaceutical composition comprising a compound of Formula I, II, III, or IV, or a pharmaceutically acceptable salt, ester, hydrate, solvate, prodrug, metabolite, analog or derivative thereof, in combination with a pharmaceutically acceptable excipient, such that ototoxicity is treated.

The present invention also provides methods for alleviating or ameliorating at least one symptom of ototoxicity by administering to a subject in need thereof a therapeutically effective amount of a pharmaceutical composition comprising a compound of Formula I, II, III or IV, or a pharmaceutically acceptable salt, ester, hydrate, solvate, prodrug, metabolite, analog or derivative thereof, in combination with a pharmaceutically acceptable excipient, such that said at least one symptom of ototoxicity is alleviated or ameliorated. Symptoms of ototoxicity include, but are not limited to, hearing loss, tinnitus, disequilibrium, Meniere's disease, vertigo, motion sickness, nausea, vomiting, ataxia, labyrinthitis, oscillopsia, dizziness, difficulty walking, and difficulty in visual tracking and processing.

The present invention also provides methods for delaying the onset or progression of ototoxicity by administering to a subject in need thereof a therapeutically effective amount of a pharmaceutical composition comprising a compound of Formula I, II, III, or IV, or a pharmaceutically acceptable salt, ester, hydrate, solvate, prodrug, metabolite, analog or derivative thereof, in combination with a pharmaceutically acceptable excipient.

The present invention also provides methods for reducing cell death or increasing cell survival of a cell from the subject suffering from ototoxicity, by administering to a subject in need thereof a therapeutically effective amount of a pharmaceutical composition comprising a compound of Formula I, II, III, or IV, or a pharmaceutically acceptable salt, ester, hydrate, solvate, prodrug, metabolite, analog or derivative thereof, in combination with a pharmaceutically acceptable excipient. Examples of a cell from the subject suffering from ototoxicity include, but are not limited to, hair cell of the cochlea, a cell of the vestibular system, a cell of the stria vascularis, or an auditory neuron.

In any of the methods of the present invention described herein, at least one second active therapeutic agent may be administered in combination with said pharmaceutical composition comprising a compound of Formula I, II, III, or IV, or a pharmaceutically acceptable salt, ester, hydrate, solvate, prodrug, metabolite, analog or derivative thereof.

The present invention also provides a pharmaceutical pack or kit for treating ototoxicity comprising one or more containers filled with a compound of Formula I, II, III, or IV, or a pharmaceutically acceptable salt, ester, hydrate, solvate, prodrug, metabolite, analog or derivative thereof in a form suitable for administration. Preferred routes of administration include intranasal and direct topical administration to the outer, middle, or inner ear.

Preferred compounds and pharmaceutical compositions include sodium (4Z,7Z,10R,11E,13E,15Z,17S,19Z)-10,17-dihydroxydocosa-4,7,11,13,15,19-hexaenoate and (4Z,7Z,10R,11E,13E,15Z,17S,19Z)-10,17-dihydroxydocosa-4,7,11,13,15,19-hexaenoic acid.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

1. Docosahexaenoic Acid (DHA) Analogs

Figure 1:
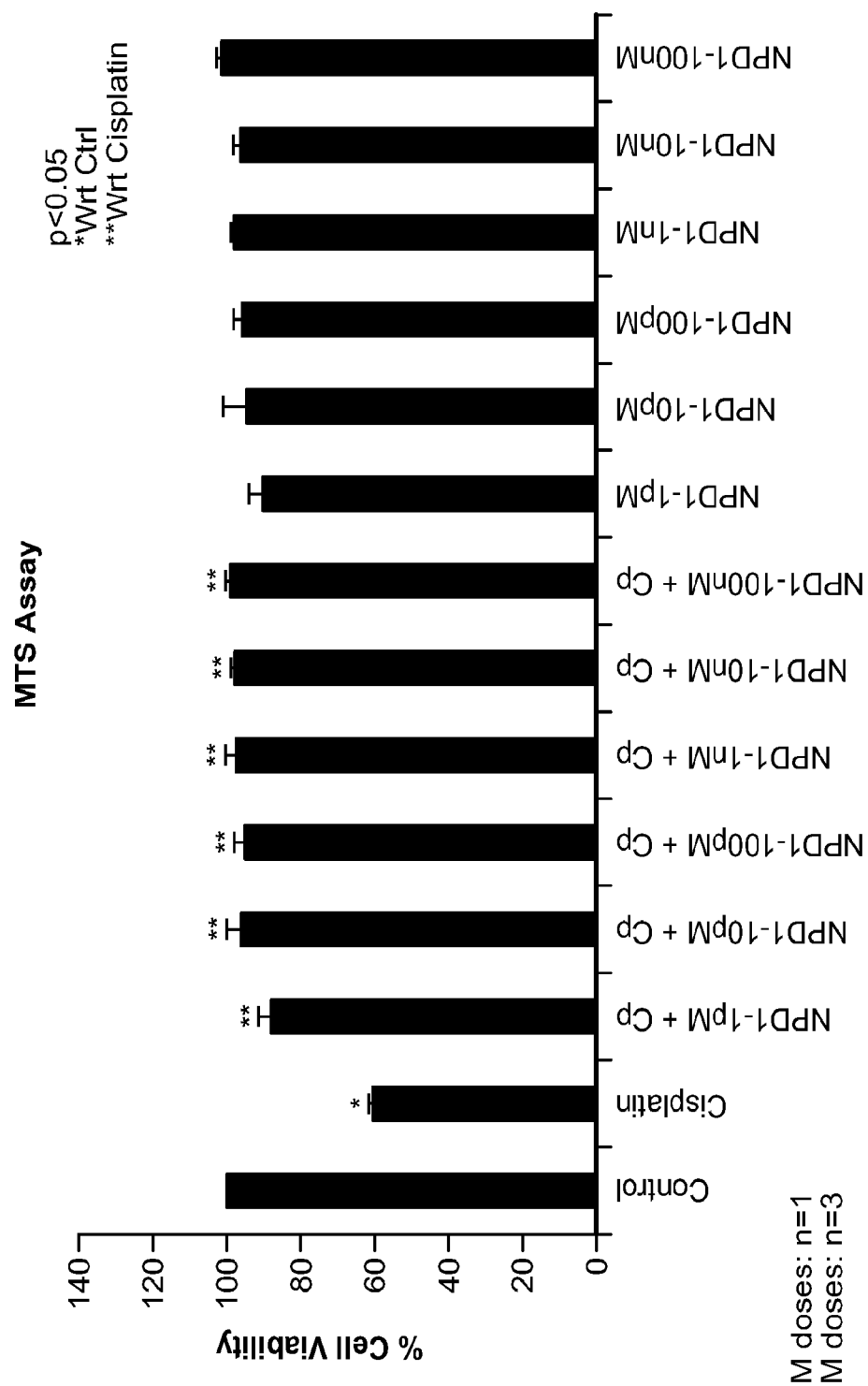
FIG. 1 is a graph showing the cell viability by MTS assay after treatment of increasing concentrations of NPD1 with and without cisplatin-induced damage.

The present, invention provides DHA analogs or their pharmaceutical compositions for use in the treatment of ototoxicity. In particular, these DHA analogs, (e.g., 10,17-dihydroxyl DHA), including isomers thereof, are isolated or purified from their natural source. Alternatively, these DHA analogs, are artificially synthesized and are optionally further purified.

The present invention relates to the compounds of Formula I:

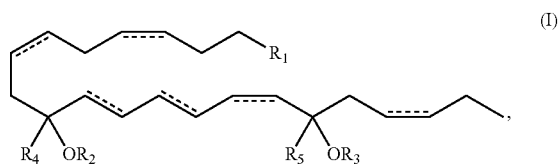

(I)

wherein:
$=$ represents a cis or trans bond;
$R_1$ is $-C(O)OR_a$, $-C(O)NR_bR_c$, $-C(O)H$, $-C(NH)NR_bR_c$, $-C(S)H$, $-C(S)OR_a$, $-C(S)NR_bR_c$, or $-CN$;
$R_2$ and $R_3$ are each independently H or a protecting group;
$R_4$ and $R_5$ are each independently H, halo, unsubstituted or substituted $C_1$-$C_6$ alkyl, unsubstituted or substituted $C_3$-$C_{10}$ carbocycle, unsubstituted or substituted heterocyclic comprising one or two 3-, 4-, 5- or 6-member rings and 1-4 heteroatoms selected from N, O and S,
$R_a$ is a protecting group or $-T_1$-$Q_1$;
$R_b$ and $R_c$ are each independently a protecting group or $-T_1$-$Q_1$, or $R_b$ and $R_c$, together with the nitrogen atom to which they are attached, form an unsubstituted or substituted heterocycle comprising one or two 5- or 6-member rings and 1-4 additional heteroatoms selected from O and S;
$T_1$ is a bond or unsubstituted or substituted $C_1$-$C_6$ alkyl linker; and
$Q_1$ is H hydroxyl, halogen, unsubstituted or substituted $C_1$-$C_6$ alkyl, unsubstituted or substituted $C_1$-$C_6$ alkoxy, unsubstituted or substituted 2-6 membered heteroalkyl, unsubstituted or substituted $C_3$-$C_{10}$ carbocycle, or unsubstituted or substituted heterocycle comprising one or two 3-, 4-, 5- or 6-member rings and 1-4 heteroatoms selected from N, O and S.

Embodiments of the invention include one or more features below.

For example, the compound used for treating ototoxicity is of formula II:

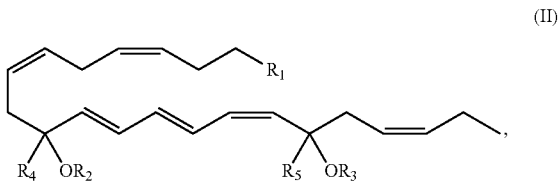

(II)

a pharmaceutically acceptable salt, ester, solvate, hydrate or prodrug thereof.

For example, the compound used for treating ototoxicity is of formula III:

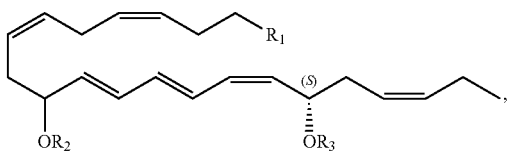

(III)

a pharmaceutically acceptable salt, ester, solvate, hydrate or prodrug thereof.

For example, in Formula I, II, or III, $R_1$ is —C(O)O$R_a$.

For example, $R_a$ is H.

For example, $R_a$ is a protecting group.

For example, in formula I, II, or III, each of $R_4$ and $R_5$ is H.

For example, at least one of $R_1$ and $R_5$ is substituted or unsubstituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, in formula I, II, or III, each of $R_2$ and $R_3$ is H.

For example, in formula I, II, or III, at least one of $R_2$ and $R_3$ is a protecting group.

For example, the compound used for treating ototoxicity is 10,17S-dihydroxydocosa-4Z,7Z,11E,13E,15Z,19Z-hexaenoic acid or a pharmaceutically acceptable salt, ester, solvate, hydrate or prodrug thereof.

For example, the compound used for treating ototoxicity is 10R,17S-dihydroxydocosa-4Z,7Z,11E,13E,15Z,19Z-hexaenoic acid or a pharmaceutically acceptable salt, ester, solvate, hydrate or prodrug thereof.

For example, the compound used for treating ototoxicity is an isolated compound, e.g., substantially separated from other compounds or isomers that are present, in a cellular environment.

For example, the isolated compound used for treating ototoxicity has a purity of at least 75%, 85%, 90, 92.5%, 95%, 97.5%, 99%, 99.5%, or 99.9% by weight.

For example, the isolated compound used for treating ototoxicity is contaminated with at most 25%, 15%, 10%, 7.5%, 5%, 1%, 0.5%, or 0.1% by weight, of other isomers of the compound.

For example, the isolated compound used for treating ototoxicity is 10,17S-dihydroxydocosa-4Z,7Z,11E,13E,15Z,19Z-hexaenoic acid or a pharmaceutically acceptable salt, ester, solvate, hydrate or prodrug thereof.

For example, the isolated compound used for treating ototoxicity is 10R,17S-dihydroxydocosa-4Z,7Z,11E,13E,15Z,19Z-hexaenoic acid or a pharmaceutically acceptable salt, ester, solvate, hydrate or prodrug thereof.

For example, the isolated compound used for treating ototoxicity is 10R,17S-dihydroxydocosa-4Z,7Z,11E,13E,15Z,19Z-hexaenoic acid or a pharmaceutically acceptable salt, ester, solvate, hydrate or prodrug thereof, and is contaminated with at most 25%, 15%, 10%, 7.5%, 5%, 1%, 0.5%, or 0.1% by weight of the 10S, 17S-enantiomer.

For example, the compound used for treating ototoxicity is an R/S racemate at C-10 carbon atom of the compound.

For example, the compound used for treating ototoxicity is an R/S racemate at C-17 carbon atom of the compound.

For example, the isolated compound used for treating ototoxicity is an R/S racemate at C-10 carbon atom of the compound.

For example, the isolated compound used for treating ototoxicity is an R/S racemate at C-17 carbon atom of the compound.

The compound useful for the method of this invention also includes those of Formula IV:

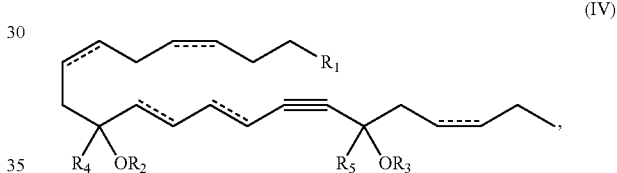

(IV)

a pharmaceutically acceptable salt, ester, solvate, hydrate or prodrug thereof. In Formula IV, ----- and $R_1$-$R_5$ are defined as above.

For example, the compound of Formula IV is an isolated compound.

Representative compounds useful for the method of the present invention include compounds listed in Table 1.

TABLE 1

| Compound Number | Structure | Name |
|---|---|---|
| 1 | 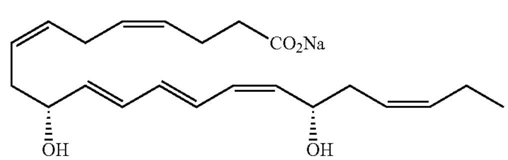 | Sodium (4Z,7Z,10R,11E,13E,15Z,17S,19Z)-10,17-dihydrodocosa-4,7,11,13,15,19-hexaenoate |
| 2 | 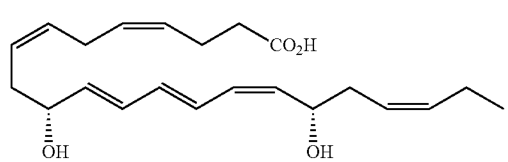 [SMILES: CC/C=C\C[C@H](O)\C=C/C=C/C=C/[C@H](O)C/C=C\C/C=C\CCC(=O)O] | (4Z,7Z,10R,11E,13E,15Z,17S,19Z)-10,17-dihydrodocosa-4,7,11,13,15,19-hexaenoic acid |

TABLE 1-continued

| Compound Number | Structure | Name |
|---|---|---|
| 3 | 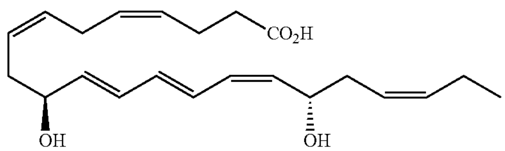 [SMILES: CC/C=C\C[C@H](O)\C=C/C=C/C=C/[C@@H](O)C/C=C\C/C=C\CCC(=O)O] | (4Z,7Z,10S,11E,13E,15Z,17S,19Z)-10,17-dihydrodocosa-4,7,11,13,15,19-hexaenoic acid |
| 4 | 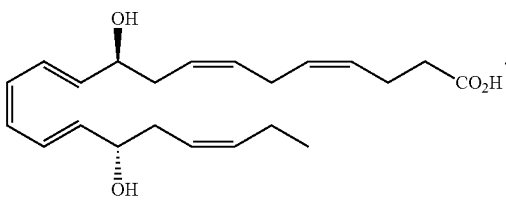 [SMILES: CC/C=C\C[C@H](O)/C=C/C=C\C=C\[C@@H](O)C/C=C\C/C=C\CCC(=O)O] | (4Z,7Z,10S,11E,13E,15Z,17S,19Z)-10,17-dihydrodocosa-4,7,11,13,15,19-hexaenoic acid |
| 5 | 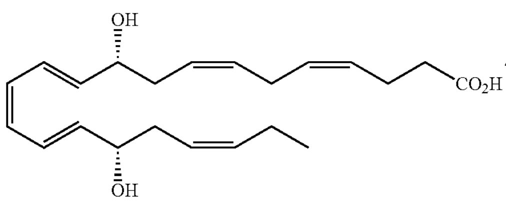 [SMILES: CC/C=C\C[C@H](O)/C=C/C=C\C=C\[C@H](O)C/C=C\C/C=C\CCC(=O)O] | (4Z,7Z,10R,11E,13E,15Z,17S,19Z)-10,17-dihydrodocosa-4,7,11,13,15,19-hexaenoic acid |
| 6 | 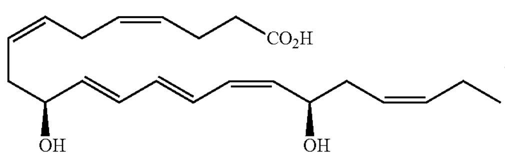 [SMILES: CC/C=C\C[C@@H](O)\C=C/C=C/C=C/[C@@H](O)C/C=C\C/C=C\CCC(=O)O] | (4Z,7Z,10S,11E,13E,15Z,17R,19Z)-10,17-dihydrodocosa-4,7,11,13,15,19-hexaenoic acid |
| 7 | 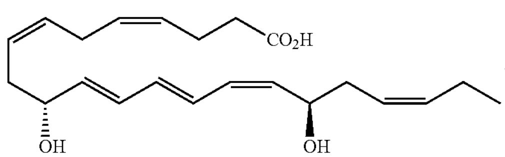 [SMILES: CC/C=C\C[C@@H](O)\C=C/C=C/C=C/[C@H](O)C/C=C\C/C=C\CCC(=O)O] | (4Z,7Z,10R,11E,13E,15Z,17R,19Z)-10,17-dihydrodocosa-4,7,11,13,15,19-hexaenoic acid |
| 8 | 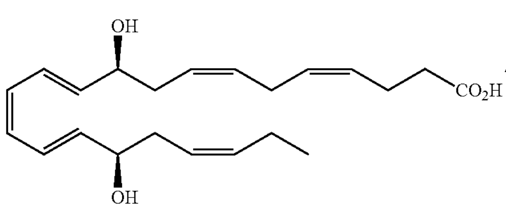 [SMILES: CC/C=C\C[C@@H](O)/C=C/C=C\C=C\[C@@H](O)C/C=C\C/C=C\CCC(=O)O] | (4Z,7Z,10S,11E,13E,15Z,17R,19Z)-10,17-dihydrodocosa-4,7,11,13,15,19-hexaenoic acid |
| 9 | 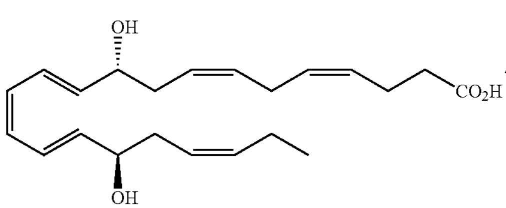 [SMILES: CC/C=C\C[C@@H](O)/C=C/C=C\C=C\[C@H](O)C/C=C\C/C=C\CCC(=O)O] | (4Z,7Z,10R,11E,13E,15Z,17R,19Z)-10,17-dihydrodocosa-4,7,11,13,15,19-hexaenoic acid |
| 10 | 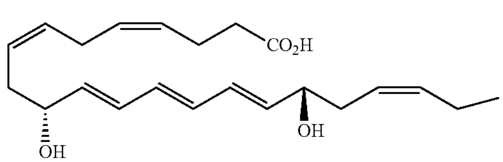 [SMILES: CC/C=C\C[C@H](O)/C=C/C=C/C=C/[C@H](O)C/C=C\C/C=C\CCC(=O)O] | (4Z,7Z,10R,11E,13E,15Z,17S,19Z)-10,17-dihydrodocosa-4,7,11,13,15,19-hexaenoic acid |

TABLE 1-continued

| Compound Number | Structure | Name |
|---|---|---|
| 11 | 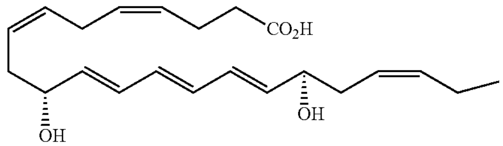 [SMILES: CC/C=C\C[C@@H](O)/C=C/C=C/C=C/[C@H](O)C/C=C\C/C=C\CCC(=O)O] | (4Z,7Z,10R,11E,13E,15Z,17R,19Z)-10,17-dihydrodocosa-4,7,11,13,15,19-hexaenoic acid |
| 12 | 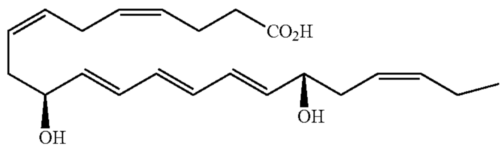 [SMILES: CC/C=C\C[C@H](O)/C=C/C=C/C=C/[C@@H](O)C/C=C\C/C=C\CCC(=O)O] | (4Z,7Z,10S,11E,13E,15Z,17S,19Z)-10,17-dihydrodocosa-4,7,11,13,15,19-hexaenoic acid |
| 13 | 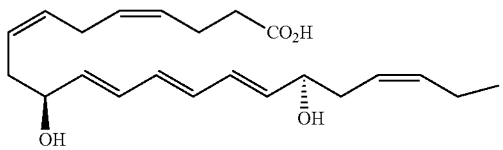 [SMILES: CC/C=C\C[C@@H](O)/C=C/C=C/C=C/[C@@H](O)C/C=C\C/C=C\CCC(=O)O] | (4Z,7Z,10S,11E,13E,15Z,17R,19Z)-10,17-dihydrodocosa-4,7,11,13,15,19-hexaenoic acid |
| 14 | 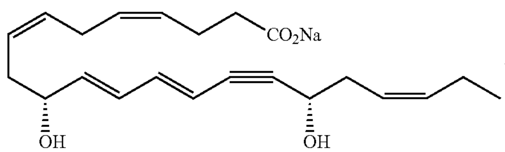 | (4Z,7Z,10R,11E,13E,15Z,17S,19Z)-10,17-dihydrodocosa-4,7,11,13,15,19-pentaen-15-ynoic acid |

The compounds that can be used for treating ototoxicity also include those omega-3 polyunsaturated fatty acid such as eicosapentaenoic acid (EPA), DHA, and their analogs (e.g., di-/tri-hydroxyl EPA or DHA) described in U.S. Pat. Nos. 7,759,395, 7,782,152, and 7,709,669, US 2009/0156673, and WO 2010/091226.

As used herein, the term "isolated compound" refers to the subject compound being purified, e.g., substantially separated from other compounds or isomers that are present in a cellular environment where resolvins are produced or that are present in crude products of synthetic chemical manufacturing processes. In certain embodiments, a purified compound is contaminated with less than 25% less than 15%, less than 10%, less than 5%, less than 2%, or even less than 1% of cellular components (proteins, nucleic acids, carbohydrates, etc.), chemical byproducts, reagents, and starting materials, and the like. In certain embodiments, a purified compound is contaminated with less than 25%, less than 15%, less than 10%, less than 5%, less than 2%, or even less than 1% of other resolvins and/or other isomers of the compound. The addition of pharmaceutical excipients, other active agents, or other pharmaceutically acceptable additives is not understood to decrease the purity of a compound as this term is used herein.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups Examples of alkyl include, moieties having from one to six carbon atoms, such as, but not limited to, methyl, ethyl, n-propyl, i-propyl, n-butyl, s-butyl, l-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

"Heteroalkyl" groups are alkyl groups, as defined above, that have an oxygen, nitrogen, sulfur or phosphorous atom replacing one or more hydrocarbon backbone carbon atoms.

As used herein, the term "cycloalkyl", "$C_3$, $C_4$, $C_5$, $C_6$, $C_7$ or cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamide), nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or of two to four carbon atoms.

As used herein, "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2$—), s-butyl (—$CHCH_3CH_2CH_2$—), i-butyl ($C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), branched alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched alkenyl group has six or fewer carbon atoms in its backbone (e.g., $C_2$-$C_6$ for straight chain, $C_3$-$C_6$ for branched chain). Likewise, cycloalkenyl groups may have from five to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Heteroalkenyl" includes alkenyl groups, as defined herein, having an oxygen, nitrogen, sulfur or phosphorous atom replacing one or more hydrocarbon backbone carbons.

The term "substituted alkenyl" refers to alkenyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched alkynyl groups, and cycloalkyl or cycloalkenyl substituted alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

"Heteroalkynyl" includes alkynyl groups, as defined herein, having an oxygen, nitrogen, sulfur or phosphorous atom replacing one or more hydrocarbon backbone carbons.

The term "substituted alkynyl" refers to alkynyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=one or two). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonyl amino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0] bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated or aromatic) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benyisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto or oxo (i.e., =O), then 2 hydrogen atoms on the atom are replaced. Keto substituents are not present on aromatic moieties. King double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent, of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, wherein oxygen, nitrogen or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkyl amino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen atom bonded to two carbon atoms or heteroatoms. For example, the term includes "alkoxyalkyl", which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls and alkthioalkynyls. The term "alkthioalkyls" include moieties with an alkyl, alkenyl or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" includes moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylamincarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

The term "amandine" or "amidinyl" includes compounds or moieties having the general structure of —C(=NR)NR'R", N(R'R")—CR(=N)—, or CR'(=NR)NR"—, in which R, R', and R" can each independently be H, alkyl, cycloalkyl, cycloalkenyl, heterocycle, aryl, or heteroaryl ect. One example of amidinyl is —C(=NH)NH$_2$. Amidines can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or N$^-$—O). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew, Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; if has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that, are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is wafer the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula I are 10,17-dihydroxyl DHA derivatives, and have Formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologicals based. Examples of carboxylic acid bioisosteres include, but are not limited to, acyl sulfonimides, tetrazoles, sulfonates and phosphonates. See, e.g., Patani and LaVoie. *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

"Protecting group": as used herein, means that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen (or hydroxyl) protecting groups include, but are not limited to methyl ethers, substituted methyl ethers (e.g., MOM (methoxymethyl ether), MTM (methylthiomethyl ether), BOM (benzyloxymethyl ether), and PMBM (p-methoxybenzyloxymethyl ether)), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, and TBDPS (t-butyldiphenyl silyl ether), esters (e.g., formate, acetate, benzoate (Bz), trifluoroacetate, and dichloroacetate), carbonates, cyclic acetals and ketals, and glycol ethers, such as ethylene glycol and propylene glycol derivatives and allyl ethers. In certain other exemplary embodiments, nitrogen protecting groups are utilized. Nitrogen protecting groups, as well as protection and deprotection methods are known in the art. Nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitroveratryloxycarbonyl ("NVOC") and the like. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" third Ed. Greene, T. W. and Wuts, P. G., Eds., John Wiley & Sons, New York: 1999, the entire contents of which are hereby incorporated by reference.

2. Synthesis of 10,17-Dihydroxyl DHA Compounds

The present disclosure provides methods for the synthesis of the compounds of Formula I-IV.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with formulae I-IV may be prepared according to the following Scheme from commercially available starting materials or starting materials which can be prepared using literature procedures. These procedures show the preparation of representative compounds of this invention.

Scheme 1

One general procedure is illustrated below.

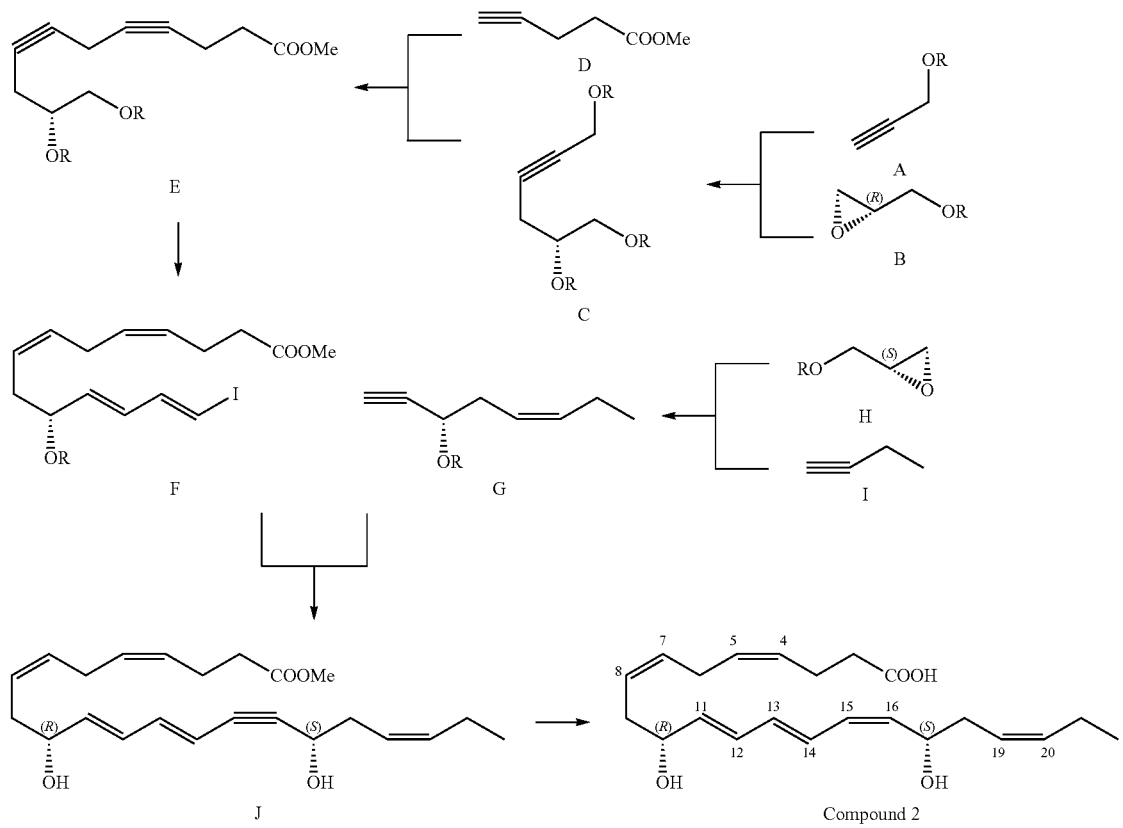

Scheme 1 above demonstrates strategy for total synthesis of Compound 2 and related isomers. The C-10 and C-17 stereochemistry of Compound 2 is derived from enantiomerically pure glycidol derivatives B and H which are reacted with alkynyl nucleophiles derived from A and I, respectively. The (Z) alkene geometry at positions 4-5, 7-8, 15-16 and 19-20 was obtained from selective hydrogenation of acetylenic precursors, which were constructed using coupling procedures. The (E) geometry at positions 11-12 and 13-14 was secured during the synthesis of intermediate F. Other stereoisomers of Compound 2 can be synthesized similarly.

Each of the stereocontrolled steps from defined precursors enabled preparation of geometric isomers of the conjugated triene region that were confirmed by NMR (see US Publication No. 2009/0156673).

3. Methods of Treatment

The present invention provides methods for treating ototoxicity in a subject in need thereof by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for the treatment of ototoxicity.

The present invention provides methods for reducing or ameliorating at least one symptom of ototoxicity in a subject in need thereof by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for reducing or ameliorating at least one symptom of ototoxicity.

The present invention provides methods for prolonging or increasing the survival of a subject suffering from, or diagnosed with, ototoxicity by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for prolonging or increasing the survival of a subject suffering from, or diagnosed with, ototoxicity.

The present invention provides methods for preventing, or delaying the onset of, ototoxicity in a subject at risk thereof by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for preventing, or delaying onset of, ototoxicity in a subject at risk thereof.

Ototoxicity is any detrimental or pathologic change in the structure or function of the outer, middle, or inner ear caused by administration of or exposure to drugs, toxins, or radiation. Many current prescribed and over-the-counter medications possess ototoxic properties. The most well-known ototoxic agents include aminoglycoside antibiotics, platinum-based antineoplastic agents, salicylates, non-steroidal anti-inflammatory drugs (NSAIDs), quinines, and loop diuretics. Other ototoxic agents include ace inhibitors, acetic acids, alpha blockers, angiotensin-2-receptor antagonists, anti-arrhythmic drugs, anti-convulsant drugs, anti-retroviral protease inhibitors, benzodiazepines, beta-blockers, bicyclic and tricyclic anti-depressants, calcium-channel-blockers, macrolide antibiotics, opiate agonist drugs, propionic acids, proton pump inhibitors, quinolones, serotonin-receptor agonists, and thiazides. Some drugs in combination with mechanical stresses (such as noise) or radiation can also cause ototoxicity in a synergistic manner.

Incidence of ototoxicity is largely unknown, due to the large number of ototoxic agents, as well as the diversity of symptoms. For example, as many as 1,200,000 people in the USA incur hearing loss each year from aminoglycosides. This statistic does not account for patients who experience other symptoms of ototoxicity, such as tinnitus, dysequilibrium, Méniè's disease, and vertigo, and therefore vastly underestimates the number of people suffering from aminoglycoside-induced ototoxicity. Up to 50% of adult patients and 75% of pediatric patients undergoing cisplatin treatment suffer from hearing loss. With the increased dependence on medications for therapy and the prevalence of ototoxicity as a side effect in many common medications, methods for treatment of symptoms caused by ototoxicity will become increasingly important.

Ototoxicity is typically associated with functional changes in hearing and balance. Generally, ototoxicity is bilaterally symmetrical (affecting both ears), but it can be asymmetrical (or unilateral) with possible development in the other ear at a later lime. The usual time of onset is often unpredictable, and marked hearing loss can occur even after a single dose of an ototoxic agent. Additionally, symptoms of ototoxicity may not manifest until several weeks or months after completion of therapy with the ototoxic agent, and severity of the symptoms may fluctuate. Ototoxicity may be reversible or may be permanent, depending on the type of medication used, dosage and duration of treatment. Some ototoxic drugs specifically damage certain structures within the ear, such as the cochlea, vestibular system, stria vascularis, and auditory/vestibulocochlear nerve (or cranial nerve VIII). The structure afflicted with ototoxicity most often dictates the symptoms the patient presents with. Furthermore, permanent hearing loss or balance disorders caused by ototoxic dings may have serious communication, educational, and social consequences.

Ototoxicity involving the cochlea produces hearing loss, usually commencing with high frequencies but often eventually progressing to the lower frequencies that encompass speech. Damage to the cochlea by ototoxic agents can include, but are not limited to, distortion of sounds, hyperacusis, auditory hallucinations, aural fullness (pressure, discomfort, or fullness sensation in the ears), other changes in auditory threshold for any stimulus, changes in perception of sound including recruitment (abnormal growth in the perception of loudness), and changes in ability to identify, localize, recognize, distinguish between, or process sounds. Cochlear damage may also manifest as tinnitus, which includes any perception of sound in the ears or inside the head that is not in response to an external signal.

Ototoxicity to the vestibular system, which includes the vestibule and semi-circular canal, manifests as balance and orientation-related disorders. These disorders include, but are not limited to, induced or spontaneous vertigo, dysequilibrium, increased susceptibility to motion sickness, nausea, vomiting, ataxia, labyrinthitis, oscillopsia, nystagmus, syncope, lightheadedness, dizziness, increased falling, difficulty walking at night, Ménière's disease, and difficulty in visual tracking and processing.

Ototoxicity can also affect any organ in the auditory or vestibular pathways from the external ear up through and including the cortex, the auditory nerve, and all pathways in between. The auditory/vestibulocochlear nerve, or cranial nerve VIII, is the least afflicted component of the ear when ototoxicity arises, however, when affected the damage is most often permanent. Damage to the auditory/vestibulocochlear nerve effectively arrests communication between the cochlear and vestibular structures and the brain. Symptoms present similar to those resulting from vestibular and cochlear damage, including tinnitus, ringing of the ears, difficulty walking, deafness, and balance and orientation issues. Damage to the stria vascularis can result in Ménière's disease, tinnitus, hearing loss, and vertigo. Ototoxicity to the outer and middle ear can cause excessive ceruminosis (ear wax production) and/or otalgia (ear pain), and may indirectly cause otitis externa or otitis media (opportunistic infections of the outer or middle ear).

The compound of the present invention can be used to treat a subject suffering from hearing loss, wherein the subject in need has been exposed to one or more toxins or ototoxic agents. There are three basic types of hearing loss: conductive, sensorineural, and mixed hearing loss. Conductive hearing loss occurs when sound does not move efficiently through the outer ear canal to the eardrum and the tiny hones, or ossicles, of the middle ear. Conductive hearing loss usually involves a reduction in sound level or the ability to hear faint sounds. Possible causes can include exposure to ototoxic agents, otitis media or otitis externa, chronic otitis media, obstruction of the external ear canal, or perforated tympanic membrane. Sensorineural hearing loss is the most common type of permanent hearing loss and occurs when there is damage to the cochlea, or to the nerve pathways from the inner ear to the brain. Possible causes can include chronic otitis media, exposure to ototoxic agents, exposure to loud noises, head trauma, or aging. Idiopathic sudden sensorineural hearing loss (ISSHL) is defined as unexplained sudden hearing loss greater than 30 dB in three contiguous frequencies and that occurs over a period of less than three days. ISSHL includes, but is not limited to: awakening with a hearing loss, hearing loss noted over a few days, selective low- or high-frequency loss, and distortions in speech perception. The degree of hearing loss is variable and is usually unilateral, but can also manifest or progress bilaterally. ISSHL can be accompanied by tinnitus (70% of patients), vertigo (50% of patients), sensation of ear fullness, and/or dizziness. There are many potential causes of ISSHL, but despite extensive evaluation, the majority of cases eludes definitive diagnosis and therefore, remains unclear. Steroids are commonly used to treat patients suffering from ISSHL. Mixed hearing loss involves the combination of conductive hearing loss with sensorineural hearing loss, caused by damage to the outer, middle, or inner ear, or the auditory nerve.

The compound of the present invention can be used to treat a subject suffering from tinnitus, wherein the subject in need has been exposed to one or more toxins or ototoxic agents. Tinnitus can be classified into two forms: objective and subjective. Objective tinnitus consists of head sounds audible to other people in addition to the subject suffering from tinnitus. The noises are generally external to the auditory system and are usually caused by vascular anomalies, repetitive muscle contractions, or inner ear structural defects. Objective tinnitus is also known as pulsatile or vascular tinnitus. Subjective tinnitus may occur anywhere in the auditory system, from the ear canal to the brain, but can only be heard by the subject. The sounds can range from a metallic or high-pitched ringing, buzzing, blowing, roaring, clicking, clanging, popping, or nonrhythmic heating. Tinnitus may be constant or occur intermittently in one or both ears. It can be accompanied by audiometric evidence of deafness which occurs in association with both conductive and sensorineural hearing loss. Other conditions and syndromes which may have tinnitus in conjunction with the condition or syndrome, are otosclerosis, Méniè's disease, and cochlear or auditory nerve lesions. Hearing loss, hyperacusis, recruitment, and balance problems may or may not be present in conjunction with tinnitus.

The compound of the present invention can be used to treat a subject suffering from dysequilibrium, wherein the subject in need has been exposed to one or more toxins or ototoxic agents. Dysequilibrium refers to unsteadiness, imbalance, or less of equilibrium; often is accompanied by spatial disorientation. Causes of disequilibrium include loss or hypofunction of the vestibular mechanisms, weakness or orthopedic difficulty of the lower extremities, and simple "dis-use" dysequilibrium, whereby a person becomes unsteady because they do not walk, exercise, or otherwise practice the skill of balance often enough. The symptoms of dysequilibrium include dizziness, sensation of disorientation, the feeling of being unsteady on one's feel, and difficulty standing or walking, particularly in the dark or in the shower. These symptoms are typically are exacerbated in situations where the vision is obstructed or if the subject experiences other conditions decreasing visual acuity. This kind of deficit usually shows dramatic improvement when the patient touches or holds onto a stationary object (e.g., replacing the loss sensitivity feel with the sensitivity of the hands). Patients with Parkinson's disease or cerebellar disease often have disequilibrium due to motor difficulties.

The compound of the present invention can be used to treat a subject suffering from Méniè's disease, wherein the subject in need has been exposed to one or more toxins or ototoxic agents. Méniè's disease affects hearing and balance to a varying degree. Méniè's disease often begins with one symptom and gradually progresses. Not all subjects suffering from Méniè's disease experience the same symptoms, however so-called "classic Méniè's" is considered to have the following four symptoms: 1) vertigo attacks that can be severe, incapacitating, unpredictable, and last anywhere from minutes to hours, and in some cases, from several days to several weeks; 2) unilateral or bilateral hearing loss, usually in lower frequencies, often initially fluctuating but eventually progressing to permanent hearing loss; 3) unilateral or bilateral tinnitus; and 4) unilateral or bilateral sensation of fullness or pressure (aural fullness). Additional symptoms that are typical of vertigo, hearing loss, tinnitus, or aural fullness may also be experienced by the subject suffering from Méniè's. Some subjects experience "drop attacks," wherein the subject experiences such extreme episodes of vertigo that they lose their balance and fall. Causes of Méniè's disease are largely unknown; however it is believed to be linked to endolymphatic hydrops, or a buildup or excess of endolymphatic fluid in the compartments of the inner ear. This endolymph buildup interferes with the normal balance and hearing signals between the inner ear and the brain. Alternatively, it has been proposed that Méniè's disease is the result of constrictions in blood vessels similar to those that cause migraine headaches. Both these causes may result from exposure to ototoxic agents. Méniè's disease may also be a consequence of viral infections, allergies, or autoimmune reactions. Méniè's disease also appears to have hereditary basis, and may be caused in part by genetic variations that cause abnormalities in the volume or regulation of endolymph fluid.

The compound of the present invention can be used to treat a subject suffering from vertigo, wherein the subject in need has been exposed to one or more toxins or ototoxic agents. Vertigo is defined as the sensation of spinning or whirling motion when one is stationary. It is a type of dizziness that is caused by a dysfunction of the vestibular system in the inner ear. Additional symptoms of vertigo include any one of the following or a combination thereof: nausea and vomiting, difficulties standing or walking, sweating, hearing loss, tinnitus, visual disturbance, weakness, difficulty speaking, a decreased level of consciousness, and abnormal eye movements. The duration of symptoms can be from minutes to hours, and symptoms can be constant or episodic. The onset may be caused by a movement or change in position. There are two types of vertigo: objective, where the subjects perceive their environment moving around them, and subjective, where the subjects feel themselves continually moving. Vertigo is also further classified into either peripheral or central, depending on the location of the dysfunction of the vestibular pathway, although it can also be established through mental thoughts. Peripheral vertigo is caused by problems with the inner ear or vestibular system. Central vertigo arises from the balance centers of the brain, it is usually milder, and has accompanying neurologic deficits, such as slurred speech, double vision, or pathologic nystagmus. The most common cause of vertigo is benign paroxysmal positional vertigo (BPPV), in which the subject suffers from brief periods of vertigo (less than one minute) that occur with changes in position. Vertigo is also known to be caused by other disorders or conditions, including, but not limited to: Méniè's disease, superior canal dehiscence syndrome, labyrinthitis, vestibular neuritis (viral infection of the inner ear), any inflammation of the inner ear as a result of the common cold, influenza, and bacterial infections, concussion, vestibular migraines, exposure to ototoxic agents, excessive consumption of alcohol, or physical trauma (e.g., skull fractures).

The mechanisms underlying ototoxicity are not fully understood and may be specific to each particular ototoxic agent, for antibiotics in the aminoglycoside class, it has been suggested that the antibiotics hind to NMDA receptors in the cochlea and damage neurons through excitotoxicity. Alternatively, other studies have suggested that aminoglycosides generate free radicals within the inner ear by activating nitric oxide synthetase and therefore increasing nitric oxide concentrations. Oxygen radicals then react with the nitric oxide to form the destructive peroxynitrite radical, which can directly stimulate apoptotic cell death. Apoptosis is mediated primarily by an intrinsic mitochondrial mediated cascade, and leads to permanent damage to the outer hair cells of the cochlea, resulting in permanent hearing loss. Loop diuretics are thought to damage the stria vascularis by inhibiting adenylate cyclase and G-proteins in the stria vascularis, thereby changing the ionic gradients between the perilymph and endolymph and causing edema. Salicylates and NSAIDs cause reversible biochemical and metabolic changes, such as decreased cochlear blood flow or reduced enzyme activity in the cochlea, rather than morphologic abnormalities. The mechanism of platinum-based cancer therapeutics, such as cisplatin, is mediated by free-radical production which damages the stria vascularis and causes outer hair cell death beginning at the basal turn of the cochlea. Free radical species are selectively produced by NADPH oxidases. The NOX family of NADPH oxidases includes, but is not limited to, XOX1, XOX3, NOX4, XOX5, DUOX1 and DUOX2. NADPH oxidases are expressed in the ear and surrounding tissues, however, XOX3 is the most highly expressed. Importantly, NOX3 produces free radical species in the inner hair cells following cisplatin exposure. The free radicals generated by this mechanism then lead to mitochondria-mediated and caspase-mediated apoptotic cell death of the inner hair cells, and ultimately permanent hearing loss.

In the methods of detecting or monitoring ototoxicity of the present invention, various parameters associated with the patient's hearing and vestibular systems can be tested by methods well known in the art to establish pretreatment baseline values and track subsequent changes. Such methods include: basic audiologic assessment, behavioral hearing test, posturgraphy, rotational tests, balance questionnaires, Romberg test, measurement of visual acuity with head movement, auditory brainstem response test (ABR), electronystagmogram (ENG), high frequency audiometry (HFA), and otoacoustic emission (OAE) measurement.

The definition and criteria for ototoxicity has been established by the American Speech-Language-Hearing Association (ASHA), the National Cancer Institute (NCI) Common Terminology Criteria for Adverse Events (CTCAE) Ototoxicity Grades, and Brock's Hearing Toss Grades. ASHA defines ototoxicity as: (a) 20 db or greater decrease in pure-tone threshold at one frequency, (b) 10 db or greater decreased at two adjacent frequencies, or (c) loss of response at three consecutive test frequencies in which responses were previously obtained, when OAE or ABR is used. Changes are always computed relative to baseline measures and must be confirmed by repeat testing, generally within 24 hours. The NCI CTCAE ototoxicity grades for children (with adult guidelines in parentheses) are as follows: Grade 1: threshold shift or loss of 15-25 dB relative to baseline, average at two or more contiguous frequencies in at least one ear (same for adults); Grade 2: threshold shift or loss of >25-90 dB, averaged at two contiguous test frequencies in at least one ear (same for adults); Grade 3: Hearing loss sufficient to indicate therapeutic intervention, including hearing aids (e.g., >20 dB bilateral HL, in the speech frequencies; >30 dB unilateral HL; and requiring additional speech language related services) (Adults: >25-90 dB, averaged at three contiguous test frequencies in at least one ear); Grade 4: Indication for cochlear implant and requiring additional speech language related services (Adults: profound bilateral hearing loss >90 dB HL). For children without baseline evaluation, baseline thresholds are assumed to be <5 dB HL. The Brock's Hearing Loss Grades, originally designed for children receiving platinum based therapeutics, are: Grade 0: Hearing thresholds <40 dB at all frequencies; Grade 1: thresholds 40 dB or greater at 8000 Hz; Grade 2: thresholds 40 dB or greater at 4000-8000 Hz; Grade 3: thresholds 40 dB or greater at 2000-8000 Hz; Grade 4: thresholds at 40 dB or greater at 1000-8000 Hz.

For early detection of ototoxic damage, such as that caused by platinum-based therapy, high frequency testing of greater than 6 kHz is preferred. Loss of the high frequency range (8.000-20,000 Hz) as a result of ototoxicity is considered increasingly important. At present, pure tone audiometry (up to 10 Hz), extended high frequency audiometry (up to 16 kHz), and distortion product emissions (up to 8 kHz) performed with conventional audiological equipment provide information on auditory function above 6 kHz. Thus, extended high-frequency audiometry is particularly useful as a high quality method to monitor and diagnose early and asymptomatic signs of ototoxicity.

Signs of ototoxicity can include, but are not limited to, reduction of the high frequency range. For example, the high frequency range of a patient suffering from ototoxicity may experience a 1%, 5%, 10%, 15%, 20%, 25%, 30%, 35%, 40%, 45%, 50%, 60%, 70%, 80%, 90%, or 100% reduction of the high frequency range compared to a person who is not suffering from ototoxicity, or compared to the same patient at an earlier timepoint. The high frequency range is, for example, greater than 6 kHz, or between about 8 and 20 kHz.

As used herein, the term "ototoxicity" includes all of the classifications of ototoxicity known in the art, including, but not limited any detrimental or pathologic change in the structure or function of the outer, middle, or inner ear caused by administration of or exposure to drugs or toxins.

As used herein, a "subject in need thereof" is a subject having ototoxicity, or a subject having an increased risk of developing ototoxicity relative to the population at large. Preferably, a subject in need thereof has been treated with one or more toxins or ototoxic agents. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, "candidate compound" refers to a compound of the present invention, or a pharmaceutically acceptable salt, prodrug, metabolite, polymorph or solvate thereof.

As used herein, "monotherapy" refers to the administration of a single active or therapeutic compound to a subject in need thereof. Preferably, monotherapy will involve administration of a therapeutically effective amount of an active compound. For example, ototoxicity monotherapy with one of the compounds of the present invention, or a pharmaceutically acceptable salt, prodrug, metabolite, analog or derivative thereof, to a subject in need of treatment of ototoxicity. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. The term "preventing" or "prevent" as used herein includes either preventing the onset of a clinically evident disease progression altogether or preventing or slowing the onset of a preclinically evident stage of a disease in individuals at risk. This includes prophylactic treatment of those at risk of developing a disease.

As used herein, the term "alleviate" or "ameliorate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Therapeutically effective dosages are expected to decrease the severity of a sign or symptom.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies surgery or physical therapy). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second active therapeutic agent. Second active therapeutic agents include but are not limited to anti-TNF inhibitors (e.g., infliximab, etanercept, adalimuinab and golimuntab), JNK inhibitors (e.g., SP600125), TRPV1 antagonists (e.g., capsazapine, AMG 9810, A784168), AMPA antagonists (e.g., NBQX, PNQX, YM-90K and ZK200775), anti-antioxidants (e.g., vitamins A, C, and E), antihistamines (e.g., meclozine, dimenhydrinate, and trimethobenzamide), antiemetics (e.g., betahistine, diazepam, and ginger root), lipoflavonoids, glutathione (GSH) or glutathione precursor (e.g. methionine, N-acetyl-DL-methionine, glutathione ethylester, glutathione diethylester, and glutathione monoethyl ester), glutathione peroxidase mimics (e.g., 2-phenyl-1,2-benzisoselenazol-3(2H)-one (ebselen), 6A,6B-diseleninic acid-6A',6B'-selenium bridged .beta.-cyclodextrin (6-diSeCD), and 2,2'-diseleno-bis-Beta-cyclodextrin (2-diSeCD)). N-acetylcysteine (NAC), resveratrol, sodium thiosulphate, allopurinol, K-phenylisopropyladenosine, alpha-tocopheral, salicylates (e.g., salicylic acid and salts of alicyclic acid), zinc salts (e.g., zinc alicylate), scavengers of peroxyl or hydroxyl radicals, calpain inhibitors, vasodilators, agonists or antagonists of the NMDA receptor, prostaglandins, prostanoid receptor agonists, protein tyrosine kinase inhibitors (e.g., Src family PTK inhibitors; non-receptor tyrosine kinase inhibitors; and non-peptide PTK inhibitors), sildenafil (e.g., sildenafil citrate), neurotrophic factors (e.g., neurturin neurotrophic factor and glial cell line derived neurotrophic factor (GDNF), amino acid derivatives (e.g., SPM927 or (R)-2-Acetamido-N-benzyl-3-methoxypropionamide), carbamazepine derivatives, tricyclic antidepressants (e.g., amitriptyline and nortriptyline), acetylcholinesterase inhibitors (e.g., donepezil and neoostigmine), receptor agonists acetylcholine esters and cholinomimetic alkaloids), opioid receptor agonists (e.g., morphine, heroin, hydromorphone, dermorphin, spiradoline, and methadone), opioid receptor antagonists (e.g., buprenorphine, butorphanol (Stadol), and nalbuphine (Nubaine)), corticosteroids, diuretics, RNA interference (RNAi) using small nucleic acid molecules to modulate expression of genes encoding proteins involved with deafness (e.g., reducing Gap Junction Beta 2 protein expression), and derivatives or combinations thereof.

Additional second active therapeutic agents which can be used in combination with the compounds of the present invention include, but are not limited to, hearing enhancement devices (e.g., hearing aids, implanted hearing devices, assistive listening and alerting devices), noise suppression devices (e.g., "white noise" machines, masking machines, and tinnitus restraining devices), hyperbaric oxygen therapy, pressure pulse treatment, surgical procedures, removal of wax buildup, vestibular rehabilitation, canalith repositioning, psychotherapy, cognitive therapy, head rest, alternative medicine (e.g., acupressure, acupuncture, and meditation), and dietary and behavioral changes.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000): Coligan et al. *Current Protocols in Immunology*, John Wiley & Sons, N.Y.; Enna et al. *Current Protocols in Pharmacology*, John Wiley & Sons, N.Y.; Fingl et al. *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

4. Pharmaceutical Compositions

The present invention also provides pharmaceutical compositions comprising a compound of Formulae I-IV in combination with at least one pharmaceutically acceptable excipient or carrier, for use in the treatment, amelioration, or prevention of ototoxicity.

A "pharmaceutical composition" is a formulation containing the compounds of the present invention in a form suitable for administration to a subject.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. A variety of routes are contemplated, including but not limited to, oral, intra-ear, pulmonary, rectal, parenteral, intradermal, transdermal, topical, transmucosal, subcutaneous, intravenous, intramuscular, intraperitoneal, intratympanic, inhalational, buccal, sublingual, intrapleural, intracerebroventricular (ICV), intrathecal, intranasal, and the like.

Solutions or suspensions used for the appropriate delivery can include the following components: a sterile diluent such as water for injection, saline solution, fixed oils, polyethylene glycols, glycerine, propylene glycol, polysorbate, tocopherol polyethylene glycol succinate (TPGS), or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. These preparations can be enclosed in ampoules, disposable syringes or multiple dose vials made of glass or plastic.

A compound or pharmaceutical composition thereof can be administered to a subject in many of the well-known methods currently used for treatments of ear disease. One such method is systemic therapy consisting of dosing medication via the oral, intravenous, or intramuscular route with the intention of altering function of the affected structure of the ear. Local administration to the afflicted structures of the ear can be achieved through topical treatments to the outer ear or intratympanic delivery for local absorption into the middle or inner ear. Intratympanic delivery can be performed through microcatheter systems, injection via syringe, hydrogel vehicles, slow release drug inserts, tubes equipped with a wick of the Silverstein Microwick type, and nanoparticle carriers. Methods for direct delivery of a compound of the present invention into the inner ear include cochlear implantation, osmotic pumps, or a reciprocating perfusion system.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated therapeutic effects, will range from about 0.0001 to about 100 mg per kilogram of body weight per day, more preferably from about 0.01 to about 50 mg per kg per day, still more preferably from about 0.1 to about 40 mg per kg per day, and even still more preferably from about 0.1 to about 1 mg per kg per day. For example, between about 0.01 microgram and 20 micrograms, between about 20 micrograms and 100 micrograms and between about 10 micrograms and 200 micrograms of the compounds of the invention are administered per 20 grams of subject weight. Generally, intratympanic doses of the compounds of this invention for a patient, when used for the indicated therapeutic effects, will range from about 0.0001 µg to about 10 mg per kilogram of body weight per day, more preferably from about 0.001 µg to about 5 mg per kg per day, and still more preferably from about 0.01 µg to about 4 mg per kg per day. Still more preferably, intratympanic doses are about 0.01 mg to about 1.0 mg. For example, about 0.1 mg is administered in a single dose to the ear.

If desired, the effective daily dose of the active compound may be administered as two, three, four, five, six or more sub-doses administered separately at appropriate intervals throughout, the day, optionally, in unit dosage forms.

The pharmaceutical compositions of the invention include a "therapeutically effective amount" or a "prophylactically effective amount" of one or more of the compounds of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the compound may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral and intratympanic compositions in dosage unit form for ease of administration and uniformity of dosage. Dosage unit, form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount for systemic administration of a compound of the invention is 0.1-20 mg/kg, more preferably 1-10 mg/kg. For intratympanic administration, a range for a therapeutically or prophylactically effective amount of a compound of the invention is 0.1-10 mg/mL. Preferably, intratympanic dosage volume will be 0.5-1.0 mL, with the range for a single dose between 0.05-10 mg. Dosage for intratympanic administration and local delivery into the middle or inner ear may be lower than the dosages required for pharmacological effect via systemic administration. Lower intratympanic dosages are preferred, as the higher doses required by systemic delivery may prohibit the mechanism of action of other medications or therapies (i.e. cancer therapy) administered simultaneously to the patient. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result ameliorating at least one symptom of ototoxicity (e.g., in slowing, and preferably regressing, the loss of hearing or development of tinnitus) and also preferably causing complete regression of ototoxicity. An effective amount of a pharmaceutical agent is that which provides an objectively identifiable prophylaxis or improvement or as noted by the clinician or other qualified observer. As used herein, the term "dosage effective manner" refers to amount of an active compound to produce the desired biological effect in a subject or cell.

For any compound, the therapeutically effective amount can be estimated initially either in cell culture assays, e.g., cochlear hair cells, or in animal models, usually guinea pigs, rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect, factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion, for intravenous or intratympanic administration, suitable carriers include physiological saline, bacteriostatic water, Cremophor EL™ (BASE, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi, the carrier can be a solvent or dispersion medium containing, for example, water, ethanol, polyol (for example, glycerol, propylene glycol, and liquid polyethylene glycol, poloxamer 407, and the like), hyaluronic acid and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In one embodiment, the preferred composition comprises the compounds of the invention and at least one excipient comprising thermo reversible properties. Of particular interest are excipients that are liquid when at room temperature and gel at higher temperatures, i.e., physiological temperature, or 37° C. Over time, the gel will slowly release the compounds of the present invention. In this manner, compositions comprising the compounds of the invention can be injected or administered, and upon delivery to the patient, the composition will gel and the compounds of the invention and/or other active ingredients will be slow-released or sustained-release to the patient over hours, days, weeks, or months. Examples of thermo-reversible excipients include, but are not limited to, poloxamer 407.

Sterile injectable solutions can be prepared by incorporating the active compound in the required amount, in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceuticals compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives, transmucosal administration can be accomplished through the use of nasal sprays or suppositories. For transdermal administration, the active compounds are formulated into ointments, salves, gels, or creams as generally known in the art.

The active compounds can be prepared with pharmaceuticals acceptable carriers that will protect the compound against rapid elimination from the hotly, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In one embodiment, the pharmaceutical composition is in bulk or in unit dosage form. The unit dosage form is any of a variety of forms, including, for example, a solution, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including but not limited to, oral, intra-ear, pulmonary, rectal, parenteral, intradermal, transdermal, topical, transmucosal, subcutaneous, intravenous, intramuscular, intraperitoneal, intratympanic, inhalational, buccal, sublingual, intrapleural, intracerebroventricular (ICV), intrathecal, intranasal, and the like.

It is especially advantageous to formulate oral, parenteral, or intratympanic compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

Dosage forms for the topical, transdermal, or intratympanic administration of a compound of this invention include ear drops, powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable sails include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetie, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactohionic, lauryl sulfonic, maleic, malic, mandelic, methane sulfonic, napsylic, nitric, oxalic, pamoic, pantothenic, phenylacetic, phosphoric, polygalacluronic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs, the terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elsevier, New York-Oxford (1985).

The compounds, or pharmaceutically acceptable salts, esters or prodrugs thereof, are administered orally, nasally, transdermals, pulmonary, inhalationally, buccally, sublingually, intra-aurally, intracochlearly, intratympanically, intraperintoneally, subcutaneously, intramuscularly, intravenously, rectally, intrapleurally, intrathecally and parenterally. In one embodiment, the compound is administered orally. In another embodiment, the compound is administered by topical administration to the inner, middle, or outer ear. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ edition. Mack Publishing Co., Easton, Pa. (1995). In an embodiment, the compounds described herein, and the pharmaceuticals acceptable salts thereof, are used in pharmaceutical preparations in combination with a pharmaceuticals acceptable carrier or diluent. Suitable pharmaceuticals acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1: NPD1 Treatment Increases Cell Viability

In the examples described herein, UB/OC-1 cells, or immortalized organ of Corti cells derived from the mouse, were utilized to examine the activity of NPD1 in the context of ototoxic damage. Treatment with cisplatin, a platinum-based chemotherapeutic, recapitulated ototoxicity damage in this model. The UB/OC-1 cells were cultured in RPMI-1640 supplemented with 10% Fetalclone-11 serum (Hyclone laboratories. Inc., Logan. Utah, USA), penicillin streptomycin and normocin (Invitrogen, Carlsbad, Calif., USA). The cultures were kept at 33° C. in an incubator with 10% CO2.

NPD1, or Compound 1 in Table 1, was analyzed for ability to increase cell viability in UB/OC-1 cells in the presence or absence of damage. In brief, 3,500 cells per well wore seeded into a 96-well plate. After 24 hours, cells were treated with varying increasing of XPD1 (1 pM, 10 pM, 100 pM, 1 nM, 10 nM, and 100 nM) alone or with Cisplatin (20 µM) for 24 hours. NPD1 treatment of 1-100 nM concentrations was tested in 3 independent experiments.

A cell proliferation assay was performed by using Cell-Titer 96® AQueous One Solution Cell Proliferation Assay Kit (Promega, Madison, Wis.), according to the manufacturer's instructions. After 24 hours, 20 µl of Cell Titer 96 AQueous One Solution reagent was added to each well in 100 µl of total volume of media. Cells were incubated for 3 to 4 hours, and absorbance was recorded at 490 nm using an ELISA plate reader. The absorbance is directly proportional to the number of living cells and is expressed as a percent relative to vehicle-treated cells.

As shown in FIG. 1, the treatment of cells with cisplatin resulted in reduced cell viability, or reduced cell proliferation. However, treatment with NPD1 in cisplatin-damaged cells increased cell viability. NPD1 treatment in cisplatin-damaged cells for all tested concentrations resulted in over 80% cell viability. Importantly, treatment with 1 nM-100 nM NPD1 resulting in over 95% viability. The increase in cell viability was statistically significant for all tested NPD1 concentrations (designated with ** in FIG. 1) with respect to the cisplatin-damaged cells. In addition, these results also demonstrate the high potency of NPD1, as treatment at 1 nM results in a similar increase in cell viability as treatment with 100 nM NPD1.

Example 2: NPD1 Treatment Increases Cell Survival

Cell survival after NPD1 treatment was also analyzed in UB/OC-1 cells in the presence or absence of damage. Specifically, cell death via apoptosis was determined by using FTTC-AnnexinV Apoptosis detection kit (BD Pharmingen, San Diego, Calif., USA) and quantified by flow cytometry. In brief, 3,500 UB/OC-1 cells per well were seeded into a 96-well plate. After 24 hours, cells were treated with varying concentrations of NPD1 (1 nM, 10 nM, and 100 nM) and 30 minutes later followed by Cisplatin (20 µM) for 24 h. At the end of the treatment time, UB/OC-1 cells were washed once with phosphate buffered saline (PBS) and harvested in a 0.5% trypsin/EDTA solution at 37° C., centrifuged at 220×g for 5 min and then immediately resuspended in the physiological buffer provided in the kit. Cells (1×10$^5$ cells/500 µl) were then maintained in the dark for 15 min at room temperature with 5 µl of both propidium iodide and FTTC conjugated annexin V, after which the samples were analyzed immediately by BD Biosciences FACSCalibur flow cytometer (San Jose, Calif.). The results were quantified using the CellQuest software (BD Biosciences, San Jose, Calif.). Data are expressed as percent viable (non-apoptotic cells) with the number of cells seeded into each well used as 100%.

Three independent experiments were performed. The results showing the percentage of cell viability (or survival) is shown in Table 2 below.

TABLE 2

Results from Flow Cytometry Analysis of Apoptosis

| | Flow Data Sep. 9, 2013 | | | | | | |
|---|---|---|---|---|---|---|---|
| | Set I Cell Viability | Set II Cell Viability | Set III Cell Viability | Avg. | Ttest | Std. Dev | SEM |
| Control - 1 | 91.78 | 80 | 96.4 | 90.69 | | 6.17 | 2.52 |
| Control - 2 | 94.28 | 87 | 94.7 | | | | |
| Cp20 um-1 | 76 | 64 | 52.4 | | | | |
| Cp20 um-2 | 46 | 59 | 61.8 | 59.87 | 0.0080 | 10.29 | 4.20 |
| NPD1-1 nM + Cp | 85 | 83 | 94.9 | 87.63 | 0.0063 | 6.37 | 3.68 |
| NPD1-10 nM + Cp | 84 | 86 | 96.5 | 88.83 | 0.0059 | 6.71 | 3.88 |
| NPD1-100 nM + Cp | 90 | 80 | 97.6 | 89.20 | 0.0023 | 8.83 | 5.10 |
| NPD1-1 nM | 96 | 96 | 98.5 | 96.83 | | 1.44 | 0.83 |
| NPD1-10 nM | 96 | 97 | 97.7 | 96.90 | | 0.85 | 0.49 |
| NPD1-100 nM | 91 | 98 | 99.5 | 96.17 | | 4.54 | 2.62 |

Figure 2:
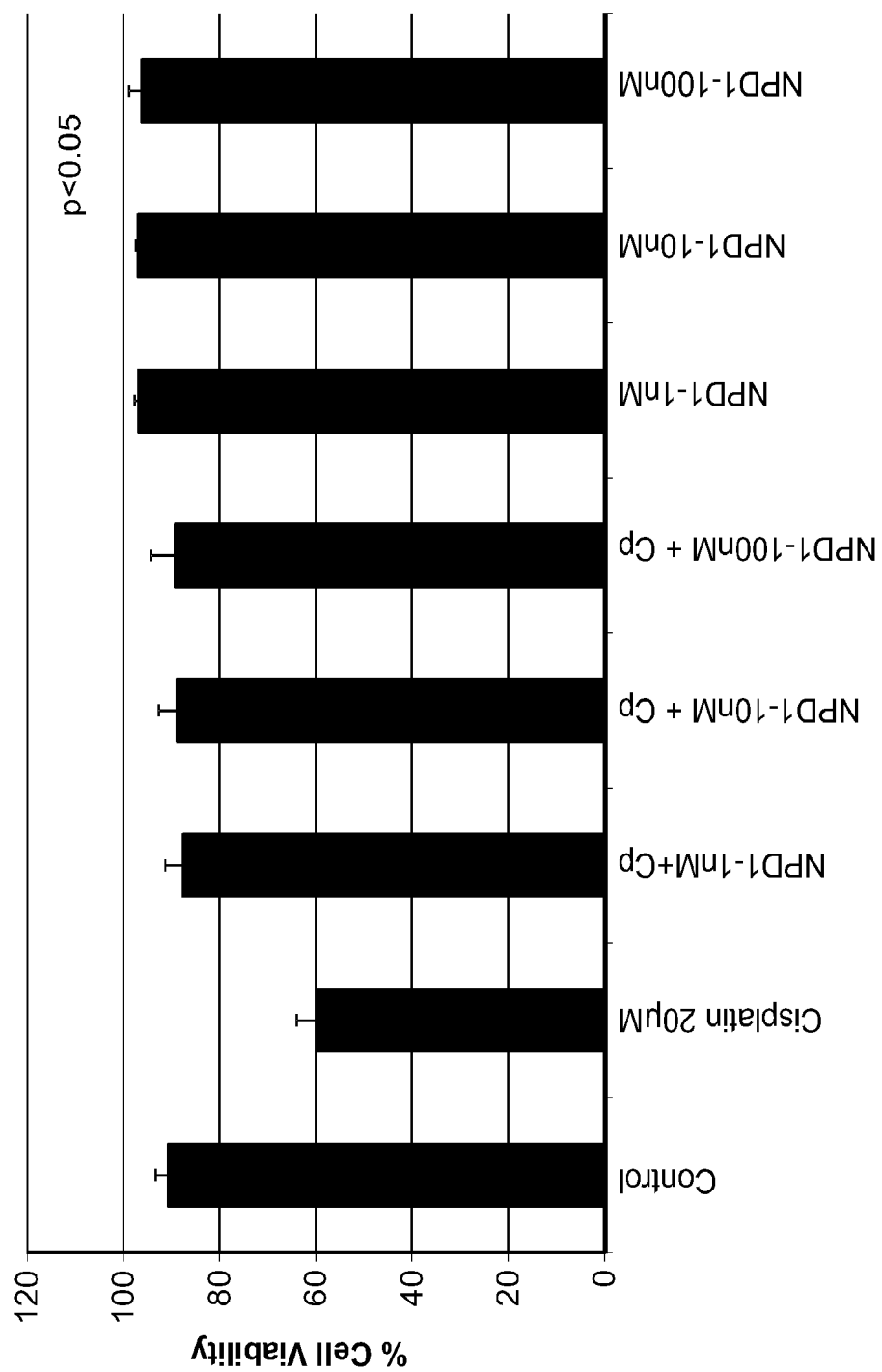
FIG. 2 is a graph showing cell viability by flow cytometry analysis after treatment of increasing concentrations of NPD1 with and without cisplatin-induced damage.

The data from Table 2 is graphically represented in FIG. 2. Cisplatin treatment caused cell viability to drop to about 60% of the total number of cell initially seeded. NPD1 treatment in cisplatin-induced damaged cells demonstrated significantly increased cell survival (i.e., over 96%) compared to cells treated with cisplatin only. These results demonstrate that treatment with NPD1 prevented or inhibited apoptosis of the cells.

Example 3: NPD1 Treatment Reduces Reactive Oxygen Species (ROS)

One of the mechanisms thought to underly the initiation and progression of ototoxicity is the generation of free oxygen radicals within the inner ear, which then interact with nitric oxide to form the destructive peroxynitrite radical that directly stimulates apoptosis. In this example, the presence of reactive oxygen species (ROS) was examined in cisplatin-induced cells after treatment with NPD1 by immunostaining.

UB/OC1 cells were cultured on glass coverslips in 12-well culture plates, 24 h later cells were pre-treated with NPD1 at various concentrations (1 nM, 10 nM and 100 nM) for 30 minutes followed by treatment with Cisplatin (2.5 µM) for 30 minutes, and then CellROX 5 µM for another 30 minutes. The cells were then washed once with phosphate buffered saline (PBS), and fixed in 4% paraformaldehyde for 15 minutes. The coverslips were then mounted with DAPI containing Vectasheild (Vector Labs, Burlingame, Calif.) Images were recorded by using a confocal microscope (LEICA confocal microscope (Buffalo Grove, Ill.) at 488 nm, and 405 nm for DAPI. CellROX is a cell-permeant dye that is weakly fluorescent while in a reduced state and exhibits bright green photo-stable fluorescence upon oxidation by reactive oxygen species (ROS) and subsequent binding to DNA. DAPI staining was used for the visualization of cell nuclei to indicate cell presence.

Figure 3:
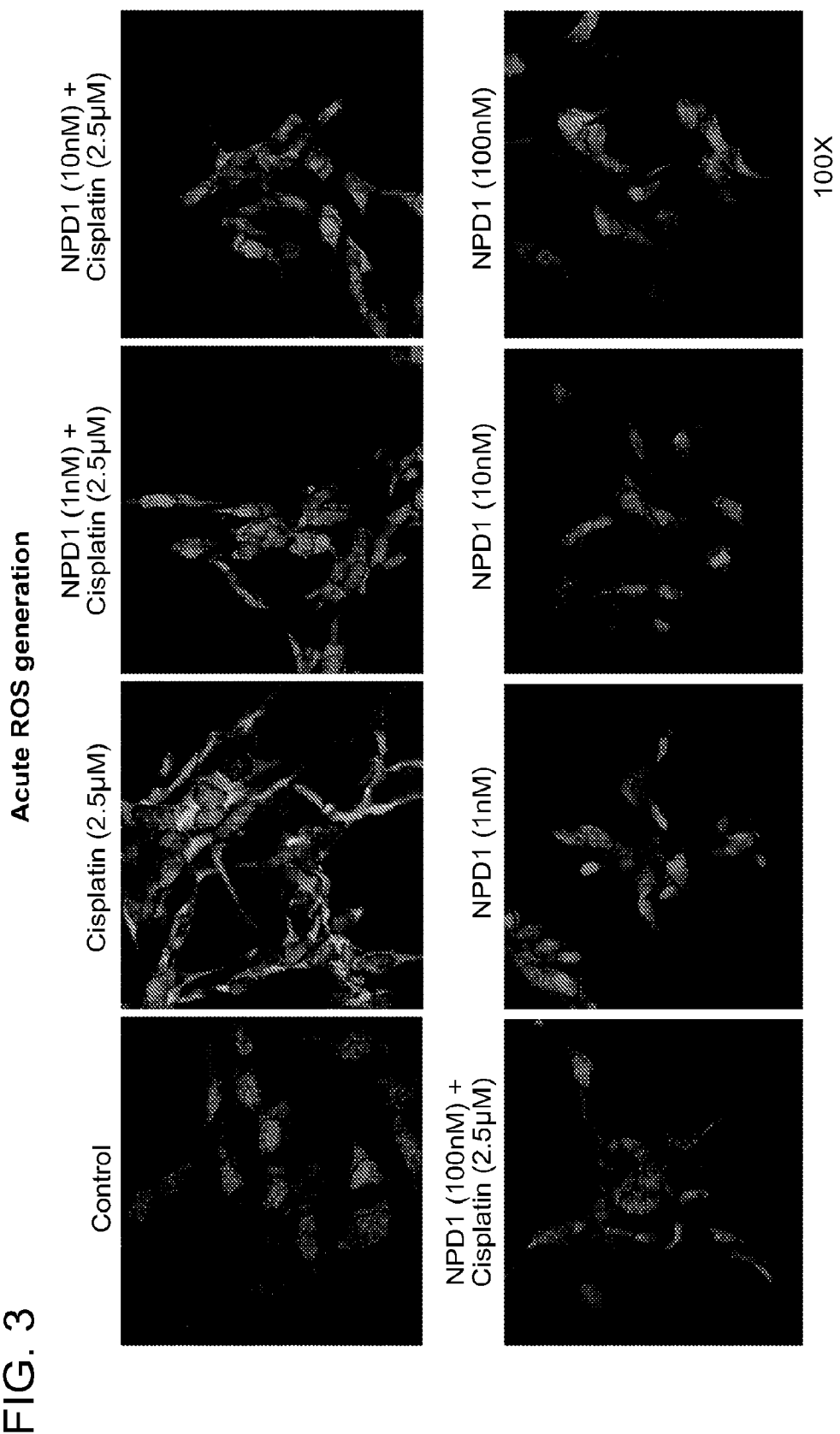
FIG. 3 is a series of immunofluorescence images showing ROS generation after treatment with NPD1 and cisplatin. Cells were stained with CellROX green reagent to detect oxidation by reactive oxygen species. Cells were also stained with DAPI for visualization of cell nuclei.

As shown in the immunofluorescence images of FIG. 3, cisplatin-damaged cells showed ROS staining in the cytoplasm of the cell. Control cells without cisplatin treatment or with cells treated with NPD1 alone showed very little or no ROS staining. The detection of presence of ROS (by staining) is expected even in the controls, as basal metabolic activity of the cell produces ROS. Treatment with NPD1 at 1 nM and 10 nM in cisplatin-damaged cells showed decreased ROS staining compared to control, while treatment with 100 nM NPD1 in cisplatin-damaged cells showed levels of ROS staining that were similar to the levels detected in control and NPD1 only treated cells. These results demonstrate that generation of ROS is inhibited or reduced upon treatment with NPD1 in damaged cells, correlating with the effect of NPD1 on promoting cell survival as described in Example 2. Importantly, treatment with NPD1 does not prohibit any basal metabolic activity that produces a basal level of ROS, further demonstrate the advantage of using NPD1 in comparison to other compounds that may inhibit the basal metabolic activity. Other compounds that may completely abrogate all ROS-producing activity may also inhibit processes that are critical for the homeostasis and normal function of these cells and/or tissues. These results demonstrate the advantage that NPD1 inhibits or reduces increased ROS production over basal levels, but does not perturn normal or cell-essential signaling.

Example 4: NPD1 Reduces Stress and Inflammatory Signaling

Ototoxicity is known to initiate stress and inflammatory pathways. Treatments that for alleviating or ameliorating symptoms of ototoxicity may also reduce stress and inflammatory signaling. Thus, stress and inflammatory markers, such as NOX3, iNOX, TRPV-1, or TNFα can also be used as markers of progression of ototoxicity.

Detection of stress and inflammatory markers in UB/OC-1 cells was performed by immunofluorescence staining. UB/OC-1 cells were first plated in a 12 well plate. After the cells adhered to the plate surface they were pre-treated with different concentrations of NPD1 (1 nM, 10 nM, and 100 nM) for 30 minutes followed by cisplatin (2.5 µM) for 24 hours. After the treatment, the cells were fixed with 4% paraformaldehyde (Sigma, St. Louis, Mo.), followed by washing once with phosphate buffered saline (PBS). Coverslips were then incubated with solution A-5% donkey serum (Jackson Immune laboratories, West Grove, Pa.) and 0.5% Triton-X (Sigma, St. Louis, Mo.) in PBS for 30 min at room temperature. Double immunostaining for different markers NOX3, iNOS. TRPV1 or TNF-α (1:300 dilution) in solution A was performed overnight at 4° C. Secondary antibody mix was then added and incubated for 1 h at 37° C. After 3 washes with PBS and two washes with fresh distilled water the coverslips were mounted on glass slides using Vectashield mounting medium containing DAPI (Vector Laboratories, Inc. Burlingame, Calif.) for nuclear staining, before imaging under an LEICA confocal microscope (Buffalo Grove, Ill.).

Figure 4:
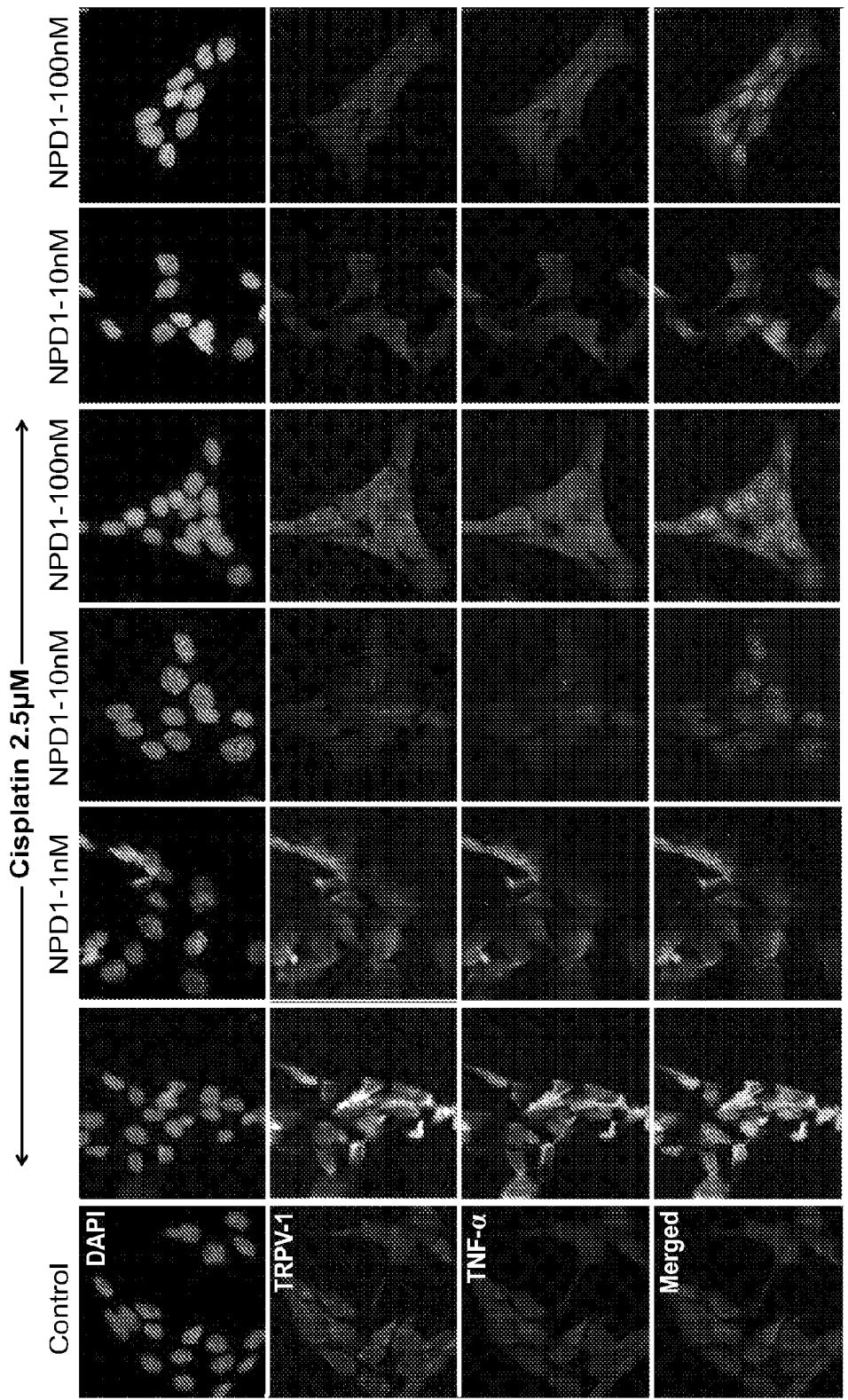
FIG. 4 is a series of immunofluorescence images showing TRPV-1 and TNFα staining after NPD1 treatment and cisplatin-induced damage. DAPI staining indicates cell nuclei. Merged images represent DAPI, TRPV-1 and TNFα staining.
Figure 5:
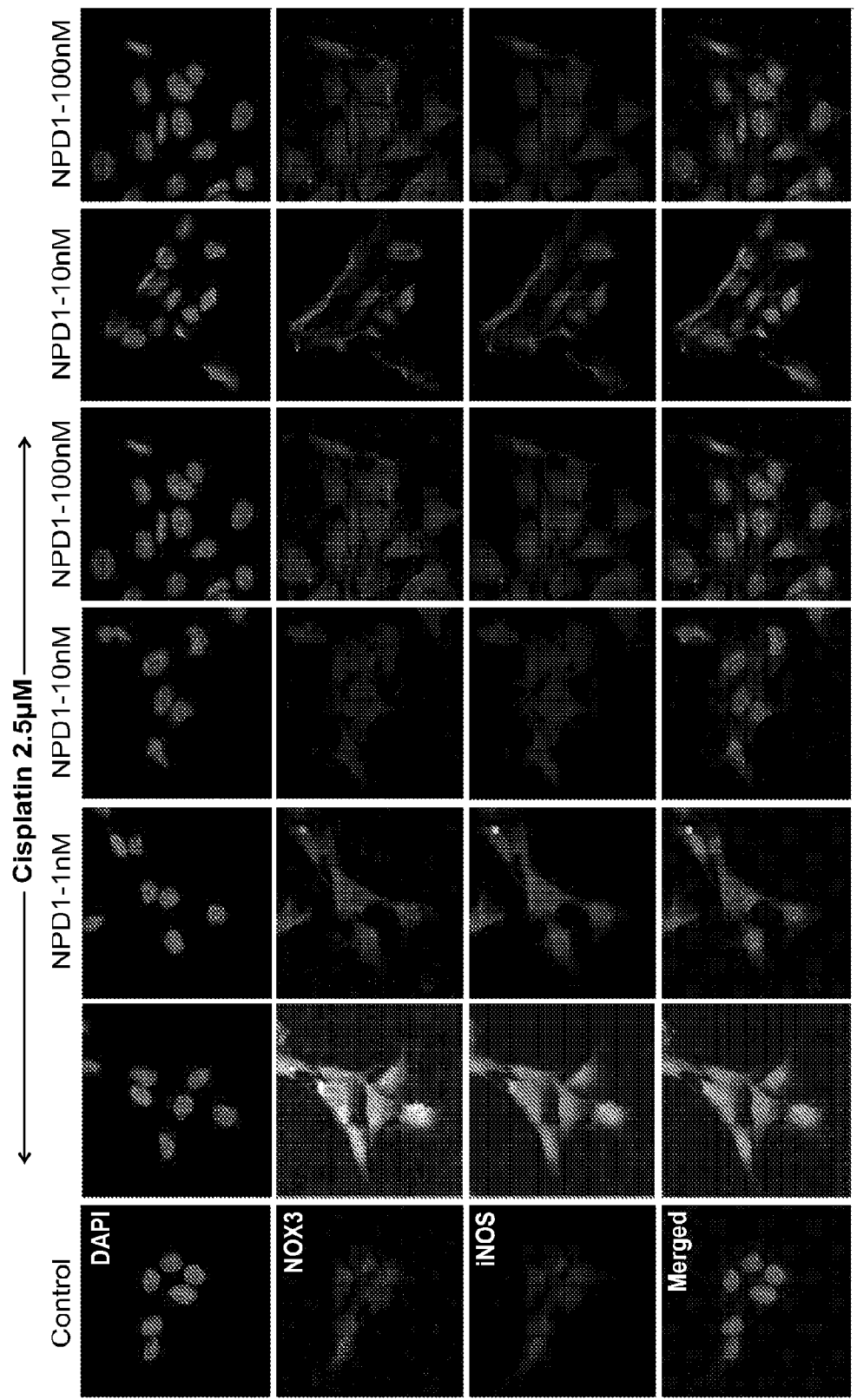
FIG. 5 is a series of immunofluorescence images showing NOX3 and iNOS staining after NPD1 treatment and cisplatin-induced damage. DAPI staining indicates cell nuclei. Merged images represent DAPI, XOX3 and iNOS staining.

Immunofluorescence images showing TRPV-1 and TNFα staining is shown in FIG. 4 and the NOX3 and iNOS staining is shown in FIG. 5. Cells were damaged by cisplatin only treatment, activating stress and inflammatory pathways as indicated by the increased staining of TRPV-1, TNFα, NOX3 and iNOS. Treatment with NPD1 in the cisplatin-damaged cells, particularly at 10 nM, showed a decrease in TRPV-1 and TNFα expression, thereby indicating a reduction in the inflammatory and stress signaling pathways. Similarly, treatment with NPD1 in the cisplatin-damaged cells at 1 nM, 10 nM and 100 nM NPD1 also resulted in a significant decrease in NOX3 and iNOS expression. Taken together, these results demonstrate that NPD1 effectively reduces the activation of inflammatory and stress pathways in response to ototoxic injury.

What is claimed is:

1. A method for treating ototoxicity comprising administering to a subject in need thereof a therapeutically effective amount of (4Z,7Z,10R,11E,13E,15Z,17S,19Z)-10,17-dihydroxydocosa-4,7,11,13,15,19-hexaenoic acid or a pharmaceutically acceptable salt thereof.

2. The method of claim 1, wherein said compound or a pharmaceutically acceptable salt thereof is in combination with a pharmaceutically acceptable excipient.

3. The method of claim 1, wherein treating ototoxicity comprises (i) delaying the onset or progression of ototoxicity; or (ii) alleviating at least one symptom or sign of ototoxicity.

4. The method of claim 3, wherein the symptom or sign of ototoxicity is selected from: hearing loss, tinnitus, disequilibrium, Meniere's disease, vertigo, motion sickness, nausea, vomiting, ataxia, labyrinthitis, oscillopsia, dizziness, difficulty walking, difficulty in visual tracking and processing, and reduction of the high frequency range.

5. The method of claim 1, wherein treating ototoxicity comprises (i) prolonging or increasing the survival of the subject suffering from ototoxicity and/or (ii) reducing cell death or increasing cell survival of a cell from the subject suffering from ototoxicity.

6. The method of claim 5, wherein the cell is a hair cell of the cochlea, a cell of the vestibular system, a cell of the stria vascularis, or an auditory neuron.

7. The method of claim 1, wherein the compound is administered at a dosage from about 0.1-1.0 mg per kg of body weight per day.

8. The method of claim 1, wherein the route of administration is selected from intraaural, intracochlear, intratympanic, and direct topical administration to the outer, middle, or inner ear.

9. The method of claim 1, wherein the compound is administered intratympanically at a dosage from about 0.01-1 mg.

10. The method of claim 1, wherein the pharmaceutically acceptable salt is a sodium salt and wherein the compound comprises (4Z,7Z,10R,11E,13E,15Z,17S,19Z)-10,17-dihydroxydocosa-4,7,11,13,15,19-hexaenoate.

* * * * *